(12) United States Patent
Munekane et al.

(10) Patent No.: US 7,404,339 B2
(45) Date of Patent: Jul. 29, 2008

(54) PROBE AND SMALL SAMPLE PICK UP MECHANISM

(75) Inventors: Masanao Munekane, Chiba (JP); Kouji Iwasaki, Chiba (JP); Takashi Konno, Takamatsu (JP); Hiroki Hayashi, Takamatsu (JP)

(73) Assignees: SII Nano Technology Inc., Chiba (JP); AOI Electronics Co., Ltd., Kagawa (JP)

( * ) Notice: Subject to any disclaimer, the term of this patent is extended or adjusted under 35 U.S.C. 154(b) by 352 days.

(21) Appl. No.: 11/182,108

(22) Filed: Jul. 15, 2005

(65) Prior Publication Data

US 2006/0010968 A1  Jan. 19, 2006

(30) Foreign Application Priority Data

Jul. 16, 2004  (JP) ............................. 2004-210199

(51) Int. Cl.
*G01N 1/00* (2006.01)
(52) U.S. Cl. ...................................... 73/863
(58) Field of Classification Search ................ None
See application file for complete search history.

(56) References Cited

U.S. PATENT DOCUMENTS

2001/0008476 A1* 7/2001 Imamura ................. 360/246.2
2005/0072231 A1* 4/2005 Chojnacki et al. ......... 73/504.14
2006/0014196 A1   1/2006 Konno et al.
2006/0220659 A1* 10/2006 Konno et al. ................ 324/662
2007/0187623 A1*  8/2007 Skidmore et al. ...... 250/492.21

FOREIGN PATENT DOCUMENTS

| JP | 2000-2630    | 1/2000  |
| JP | 2001-83055   | 3/2001  |
| JP | 2002-33366   | 1/2002  |
| JP | 2002-333387  | 11/2002 |

OTHER PUBLICATIONS

U.S. Appl. No. 60/505,026.*

* cited by examiner

*Primary Examiner*—Robert R Raevis
(74) *Attorney, Agent, or Firm*—Brinks Hofer Gilson & Lione

(57) ABSTRACT

A probe mechanism and a sample pick up mechanism of the invention are provided at an observing apparatus or an analyzing apparatus and characterized in including a tip member comprising a needle-like member brought into contact with a sample, including a driving electrostatic actuator and means for monitoring a change in an electrostatic capacitance between electrodes of the electrostatic actuator, and capable of sensing that the probe is brought into contact with a sample by the monitor.

28 Claims, 4 Drawing Sheets

SMALL SAMPLE PICKING UP METHOD

TWEEZERS USING ELECTROSTATIC ACTUATORS

TWEEZERS USING ELECTROSTATIC ACTUATORS (WITH ELECTRODES OF TIPS)

PROBE AND SMALL SAMPLE PICK UP MECHANISM

This application claims priority under 35 U.S.C. § 119 to Japanese Patent Application No. 2004-210199 filed Jul. 16, 2004, the entire content of which is hereby incorporated by reference.

BACKGROUND OF THE INVENTION

The present invention relates to a probe mechanism constituted by a tip member comprising a needle-like member brought into contact with a sample, and a pick up mechanism having a handling function of separating, picking up, storing or the like of a small sample, particularly a pick up mechanism highly convenient for cutting out a defect portion of a sample of a transmission electron microscope (TEM) or a semiconductor device which are attached to an analyzing apparatus of a focusing ion beam (FIB) apparatus or a scanning probe microscope (SPM).

There is carried out an operation of bringing a probe into contact with a sample while observing the sample by a scanning electron microscope (SEM), a scanning ion microscope (SIM), or a scanning probe microscope (SPM) and inspecting a physical property of an electric property or the like thereof. Further, there is carried out an operation of cutting out and picking up a portion of a semiconductor wafer or the like to fix to a sample base or the like in picking up a TEM sample or cutting out a failed defect portion thereof. The operation is constituted by a series of operation of making a needle-like probe approach a specific portion of a sample by operating a manipulator, bringing a probe tip portion into contact therewith and thereafter fixedly attaching the probe tip portion thereto by deposition (CVD) by FIB, further cutting to separate a sample piece from a sample main body by FIB etching, thereafter, carrying a sample piece to a predetermined position at which a sample base or the like is present to fix by operating the manipulator, and subjecting the tip portion of the probe fixedly attached with the sample piece previously by CVD to FIB etching to cut to separate the sample piece while observing in a chamber of an FIB apparatus or the like.

Patent Reference 1 discloses a technology of separating a sample piece including a region to be observed from a sample board by an ion beam sputtering method, picking up the sample piece from the sample board by using a beam member comprising a rod-like member for holding the sample piece by a force by elastically deforming a portion thereof for pressing to hold the sample and drawing to separate the sample, having a shape of a tip slenderer than a root thereof and dividing the tip portion for holding the sample piece provided by the shape, moving the sample piece to a mounting base for mounting the sample piece and separating the beam member and the sample piece to store the sample piece with an object of providing an apparatus and a method of separating, picking up and storing the small sample piece firmly and stably without contaminating the small sample piece and a peripheral region thereof. The invention adopts a mode of grabbing the sample piece in a tweezers mode by pinching the sample piece by a divided portion to press and therefore, although it is not necessary to fixedly attach the probe and the sample piece by CVD to thereby shorten an operation time period in comparison with the background art, a considerable skill is needed in the operation of pinching the sample piece by operating a manipulator while observing the sample piece by the microscope. Further, depending on a size or a shape of the sample, a size and a shape of the divided portion needs to be changed and the sample piece may be damaged by exerting an unreasonable force in pinching the sample piece.

Figure 5:
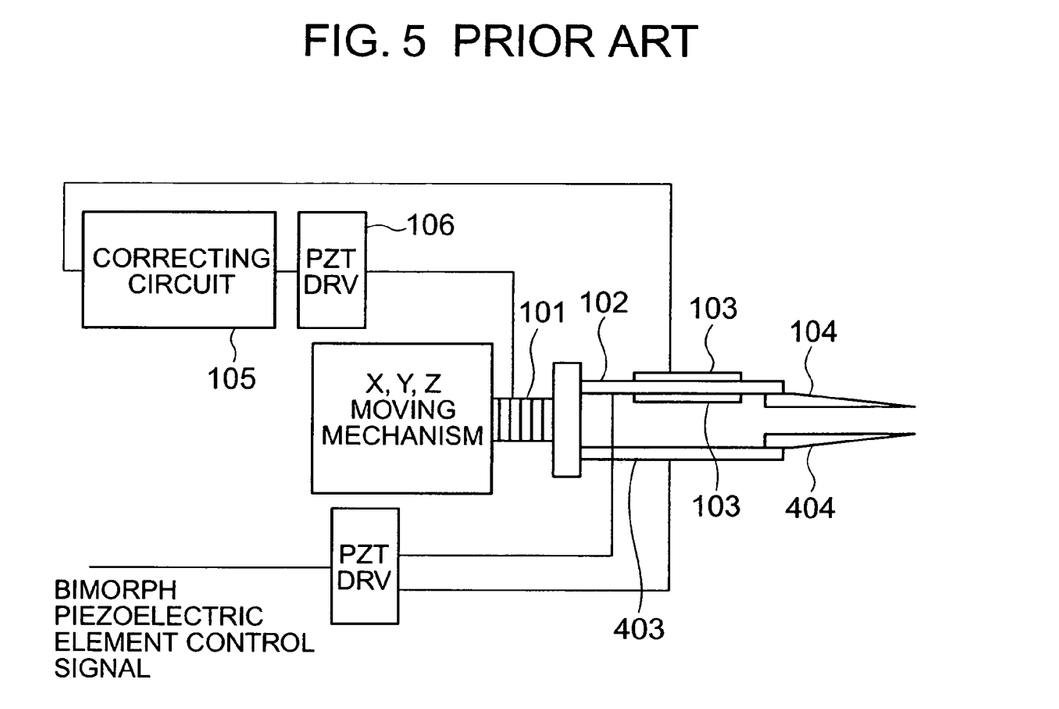
FIG. 5 is a view for explaining a pick up mechanism driven by a bimorph type piezoelectric element adopted in an FIB apparatus of a background art.

Further, Patent Reference 2 discloses a pair of microtweezers in which as shown by FIG. 5, bimorph type piezoelectric elements 102, 403 are arranged in a direction of elongating and contracting a laminated type piezoelectric element 101, a correction amount 112 is generated by strain gage elements 103 pasted on both faces of the bimorph type piezoelectric element and a correcting circuit 105, and by elongating and contracting the laminated type piezoelectric elements, loci of moving tips of probes 104, 404 are linearly displaced with an object of providing a probe moving apparatus, a microtweezers apparatus having excellent operability applicable also to fine operation by automatically correcting a deviation in a circumferential direction centering on a fulcrum of the bimorph type piezoelectric element produced by bending the bimorph piezoelectric element. The microtweezers pick up a small body of a micrometer level by utilizing a fact that an interval between the tips of the small probes is narrowed by applying a voltage to both or one of the bimorph type piezoelectric elements. By the constitution, the interval between the tips of the small probes 104, 404 can be controlled without positional shift and therefore, there is achieved an effect of capable of accurately and easily picking up a small body. Although according to the method, it is not necessary to fixedly attach the probe and the sample piece by CVD, not only the operational time period is shortened in comparison with the background art but also the grabbing operation is simple since the tweezers drive mechanism is provided, further, the sample piece is not damaged since the unreasonable force is not exerted thereto, the piezoelectric element is used as the drive source and therefore, it is necessary to connect a high voltage power source in driving the microtweezers, which is not preferable in handling a semiconductor sample or a living body sample. Further, a state of bringing the sample and the probe into contact with each other is obliged to confirm by microscope observation.

A technology of sensing contact between the probe and the sample is disclosed in Patent Reference 3 or Patent Reference 4. The invention of Patent Reference 3 is a technology of improving Patent Reference 2, it is an object thereof to provide inexpensive contact sensing means capable of sensing the contact of the sample and the probe regardless of a kind of the sample, and a probe comprising a needle-like conductive material having a tip in an acute angle shape is fixedly attached to a free end of a warp sensing beam having a piezoelectric resistance layer a resistance value of which is changed in accordance with a deformation of its own. Although contact between the sample and the probe can be sensed by adopting such a constitution, the constitution poses a problem that the sensing is limited in a direction of laminating piezoelectric elements. Further, it is an object of the invention of Patent Reference 4 to provide a probe apparatus capable of detecting that a small sample is completely cut off when a small sample is cut off from a sample of a wafer or the like to pick up by a probe, and it is detected that the small sample is completely cut off by previously applying a probe voltage from a probe control portion to the probe and detecting a change in the probe voltage immediately after cutting off the small sample from the sample by FIB. According to the contact sensing method, it is necessary to make a current flow in the sample and therefore, the method is based on a condition that the sample is conductive and the method is not applicable to a sample damaged, or destructed or the like by conducting electricity.

[Patent Reference 1] JP-A-2002-333387 "Beam member and sample machining apparatus and sample pick up method using beam member" Publication date; Heisei-14-11-22 (Nov. 22, 2002)

[Patent Reference 2] JP-A-2000-2630 "Probe moving apparatus and sample fabricating apparatus using the same" Publication date; Heisei-12-1-7 (Jan. 7, 2000)

[Patent Reference 3] JP-A-2002-33366 "Probe unit and sample operating apparatus using the same" Publication date; Heisei-14-1-31 (Jan. 31, 2002)

[Patent Reference 4] JP-A-2001-83055 "Probe apparatus" Publication date; Heisei-13-3-30 (Mar. 30, 2001)

A problem to be resolved by the invention resides in providing a probe mechanism or a small sample pick up mechanism of analyzing apparatus overcoming the above-described drawbacks of the mechanism of the background art, that is, providing a mechanism having a function of sensing contact of a sample and a probe without damaging the sample in approaching the sample, enabling to handle swiftly and firmly a small sample as a pick up mechanism and structurally simple without selecting a material of the sample.

SUMMARY OF THE INVENTION

According to the invention, there is provided a probe mechanism provided at an observing apparatus or an analyzing apparatus and characterized in including a tip member comprising a needle-like member brought into contact with a sample, the needle-like member comprising an electrostatic actuator for driving, and means for monitoring a change in an electrostatic capacitance between electrodes of the electrostatic actuator and capable of sensing that the needle-like member is brought into contact with the sample by the monitor.

According to the invention, the probe mechanism is installed in a vacuum chamber for an observing, analyzing or machining apparatus having a charged particle lens-barrel.

According to the probe mechanism of the invention, a structure of the electrodes of the electrostatic actuator is formed by a combteeth shape to intensify a drive force and promote a contact sensitivity.

According to the invention, there is provided a sample pick up mechanism provided at an observing apparatus or an analyzing apparatus and characterized in including a tip member comprising two pieces of needle-like members for grabbing a sample, comprising an electrostatic actuator for driving to make the two pieces of needle-like members proximate to and separate from each other, and means for monitoring a change in an electrostatic capacitance between electrodes of the electrostatic actuator to be capable of sensing that the needle-like members are brought into contact with the sample by the monitor.

Further, according to the invention, the sample pick up mechanism is installed in a vacuum chamber of an observing, analyzing or machining apparatus having a charged particle lens-barrel so as to be able to observe and machine by the changed particle.

Further, according to the sample pick up mechanism of the invention, a structure of the electrodes of the electrostatic actuator is formed in a combteeth shape in order to intensify a drive force and promote a contact sensitivity.

According to the sample pick up mechanism of the invention, there is adopted a structure of aligning positions of the two pieces of needle-like members at a center thereof, arranging the electrostatic actuators in a shape of a flat plate to interpose the two pieces of needle-like members on both sides thereof and connecting the electrostatic actuators and the two pieces of needle-like members locally by a coupling member. Further, the probe of the needle-like member and the electrostatic actuator are connected by interposing an insulating layer therebetween.

According to an electrostatic actuator installed at the probe of the invention and the sample pick up mechanism of the invention, a structure of including the needle-like member and the electrode is fabricated by a semiconductor silicon process technology.

According to the invention, there is provided a method of picking up a sample comprising a step of making a needle-like member approach a sample along with an electrostatic actuator while observing the sample by a microscope, a step of sensing that the needle-like member is brought into contact with the sample from a change in an electrostatic capacitance of the electrostatic actuator shown in a monitor, a step of grabbing the sample by driving the electrostatic actuator when it is sensed that the needle-like member is brought into contact with the sample, and a step of picking up the sample after grabbing the sample by using an observing, analyzing or machining apparatus including the electrostatic actuator for driving to make two pieces of the needle-like members for grabbing the sample proximate to and remote from each other, and the means for monitoring the change in the electrostatic capacitance between electrodes of the electrostatic actuator.

According to the invention, there is provided a method of analyzing an electric property of a surface of a sample comprising a step of sensing that a probe is brought into contact with the sample from a change in an electrostatic capacitance of an electrostatic actuator shown by a monitor, and a step of detecting an electric property of a portion of the sample brought into contact with the probe when it is sensed that the probe is brought into contact with the sample by a detecting portion electrically connected to the portion by way of the probe by using a sample pick up mechanism including the means for monitoring the change in the electrostatic capacitance between electrodes of the electrostatic actuator and connecting the probe of a needle-like member and the electrostatic actuator by interposing an insulting layer therebetween.

The probe mechanism and the small sample pick up mechanism of the invention are constituted by including the electrostatic actuator for driving and the means for monitoring a change in the electrostatic capacitance between the electrodes of the electrostatic actuator and therefore, the electrostatic actuator brings the tip member into contact with the sample and drives to grab the sample and therefore, the voltage necessary for driving to displace the tip by the same amount is far smaller than that in piezoelectrically driving the tip of the background art in the scale. Further, when the probe or the two pieces of needle-like members are brought into contact with the sample in a procedure of approaching the sample, the reaction is received thereby, and the contact can be sensed by the function of monitoring the change in the electrostatic capacitance. Thereby, the operation while observing the sample by FIB, SEM or the optical microscope is facilitated and efficient.

Further, the structure of the electrodes of the electrostatic actuator according to the invention is formed by the combteeth shape and therefore, the electrostatic capacitance can be increased by increasing areas of the electrodes opposed to each other, the driving force of the actuator is increased and the electrostatic actuator can function as a three-dimensional touch sensor with excellent sensitivity.

Further, by adopting the electrostatic actuator including the needle-like member and the electrode structure fabricated by the silicon process technology, the electrostatic actuators with excellent accuracy can be provided comparatively inexpensively by the large amount and can correspond also to a frequent interchanging demand.

The small sample pick up mechanism of the invention adopts the structure of arranging the two pieces of needle-like members at the center and the electrostatic actuators in the shape of the flat plate to interpose the two pieces of needle-like members on both sides thereof and connecting the two pieces of needle-like members and the electrostatic actuators locally by the coupling member and therefore, the two pieces of needle-like members can be operated to drive to be proximate to and remote from each other steadily by low energy.

Further, according to the small sample pick up mechanism of the invention, the insulting layers are interposed at the coupling members for connecting the needle-like members and the electrostatic actuators and therefore, a voltage or the like applied on the driving portion is not applied to the sample and the sample is not damaged electrically.

According to the method of picking up a sample of the invention, in a procedure of making the needle-like member approach the sample for each of the electrostatic actuators while observing the sample by the microscope, it is sensed that the needle-like member is brought into contact with the sample from a change in the electrostatic capacitance of the electrostatic actuator shown in the monitor and therefore, the operation of grabbing the sample by driving the electrostatic actuator can easily and firmly be executed.

Further, the method of analyzing the electric property of the surface of the sample of the invention can be executed in the state in which the voltage or the like applied on the electrostatic actuator driving portion is not applied to the sample and the sample is not electrically damaged since connection between the needle-like member and the electrostatic actuator is insulated. Further, it is sensed that the probe is brought into contact with the sample from a change in the electrostatic capacitance of the electrostatic actuator shown in the monitor and therefore, after confirming that the surface of the sample and the probe are brought into contact with each other, the electric property of the portion can easily and firmly be detected by the detecting portion electrically connected thereto by way of the needle-like member.

DETAILED DESCRIPTION OF THE INVENTION

The inventors have developed a "gripper" capable of accurately moving an arm and capable of firmly grabbing even a small sample of a micrometer order and filed an application thereof on a date the same as that of the present application. The gripper is a structure having an electrostatic actuator for driving to make a pair of arms having parallel grabbing faces proximate to and remote from each other while maintaining the grabbing faces in parallel with each other and is fabricated as a small structure by using a semiconductor silicon process technology. The invention has conceived to adopt such a gripper at a grabbing portion of a pick up mechanism in an analyzing/observing apparatus of FIB or SEM which needs to handle the small sample in order to resolve the above-described problem. That is, in an analyzing apparatus which observes and inspects a small sample of the invention the invention has been developed to provide a mechanism which enables to handle a small sample safely, swiftly and firmly as a pick up mechanism and is structurally simple without selecting a material of the sample and a first characteristic point thereof resides in adopting an electrostatic actuator in place of a piezoelectrically driven actuator which has been used in the pick up mechanism of the background art. By replacing the drive source of the actuator, it is not necessary to apply a high voltage at a vicinity of the sample and a voltage which is needed in driving to the same degree becomes far smaller in a scale thereof.

Further, a second characteristic point of the invention resides in providing a function of monitoring an electrostatic capacitance between electrodes. According to the constitution, when a probe is brought into contact with an object (sample) in a procedure of being drive by an electrostatic actuator, as a reaction thereof, the electrostatic capacitance in correspondence with a displacement between the electrodes is discontinuously changed. When the change is monitored by an electrostatic capacitance sensor, contact of the probe can be sensed. According to observing, machining and analyzing apparatus of the background art, the operation is made to proceed while observing a state of a sample, for example, a sample and a state of bringing a pick up probe into contact with the sample by a microscope. However, although a microscope image is a two-dimensional image and therefore, the firm contact cannot be confirmed, according to the invention, by monitoring the contact by the electrostatic capacitance sensor, the contact state can accurately be sensed, thus an efficiency of the operation is promoted and the sample is not damaged in approaching the sample.

Figure 1:
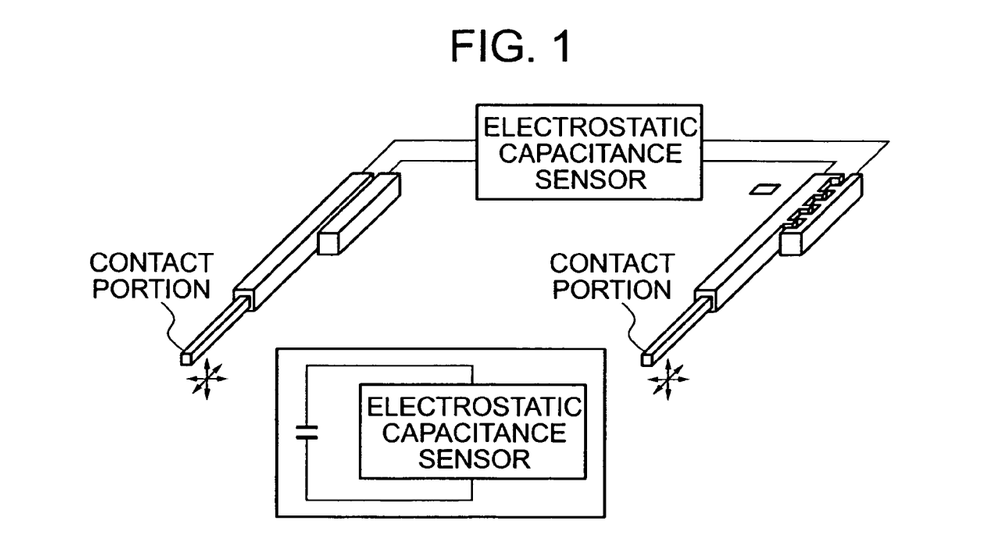
FIG. 1 is a view showing a basic constitution of a probe mechanism of the invention having an electrostatic actuator and an electrostatic capacitance sensor.

FIG. 1 shows a principle view of a probe attached with an electrostatic actuator according to the invention. The probe is conceived to be brought into contact with the surface of the sample and detect, for example, an electric property or the like of a portion rather than to pick up the sample. According to a probe shown on the left side, a probe comprising a needle-like member is integrally attached fixedly to one side of a pair of electrodes. Assuming that the electrode on other side is fixed to an apparatus side, when different charges are applied between the two electrodes, an attraction force is operated to the two electrodes and the probe is displaced to the other electrode side. On the other hand, when the same charges are applied, a repulsion force is operated to the two electrodes and the probe is displaced to be remote from the other electrode. Although the operation is nothing but the operation of the electrostatic actuator of the background art, the invention not only supplies the charges between the electrodes but also is provided with the electrostatic capacitance sensor for monitoring the electrostatic capacitance between the electrodes and therefore, when the probed is displaced, the electrostatic capacitance is changed in accordance therewith and the displacement can be sensed. When the probe is driven by a manipulator or the like and is brought into contact with an object (sample), the probe receives a reaction thereof in being driven to displace. The reaction can be detected by the electrostatic capacitance sensor as a change in the electrostatic capacitance. A correspondent operation of stopping to drive the actuator or the like can be carried out by determining that the probe is brought into contact with the sample by detecting the signal. Detection of contact is monitored by the change in the electrostatic capacitance and therefore, different from a type of making a current flow to the sample as in the background art, the contact can be detected without electric breakdown or temperature rise.

Under a condition of a probe having a small structure for an analyzing apparatus which is obliged to be arranged in a narrow space, according to a simple mode of constituting the two electrodes by a pair of planes opposed to each other, not only a problem that a drive force cannot sufficiently be exerted is posed but also a sensitivity when the direction of the reaction received by the contact is in parallel with the electrode planes becomes low. Hence, according to the invention, it is conceived that the two electrodes are formed in a combteeth shape as shown by the right side of FIG. 1. By forming the electrode structure in the combteeth shape in this way, when the tip is brought into contact with something, the electrostatic capacitance can be sensed by a change in a sectional area S. The detection is effective not only in an up and down direction but also in a horizontal direction in principle thereof, three-dimensional contact can be sensed different from one direction contact as in a touch sensor of a piezoelectric type of the background art although a direction thereof cannot be discriminated. Further, when the two electrodes are formed by the combteeth shape, areas of the electrodes opposed to each other are increased, the electrostatic capacitance can be increased and the drive force of the actuator can be increased and the sensitivity as the touch sensor can be promoted.

Figures 2A, 2B:
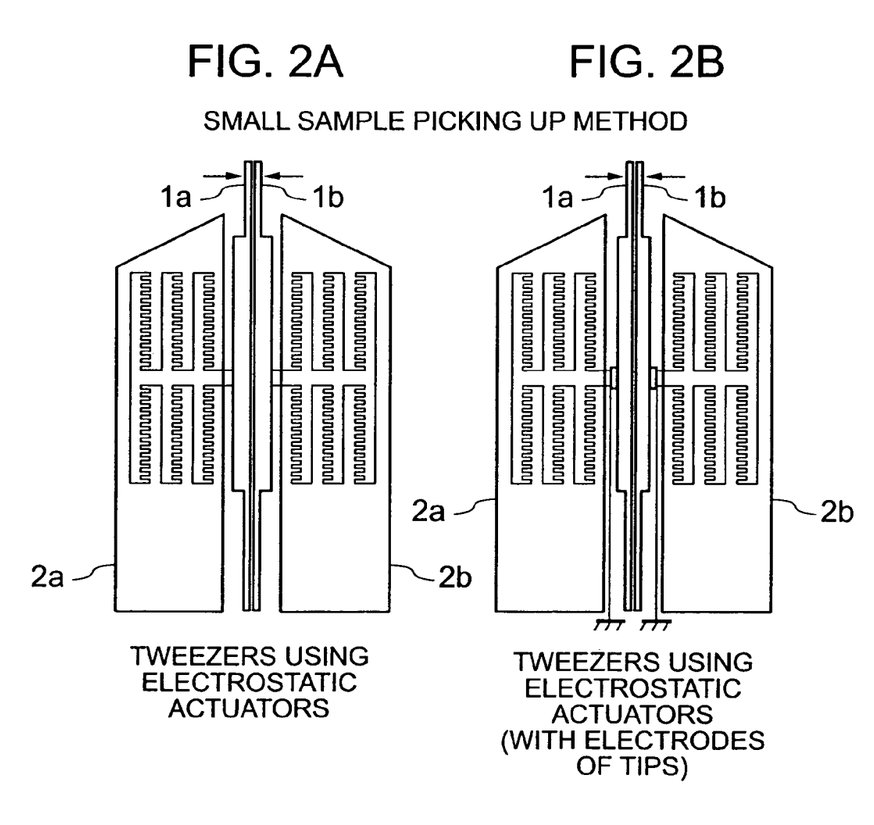
FIGS. 2A-2B illustrate views showing a basic constitution of a pick up mechanism of the invention having two pieces of needle-like members for grabbing a small sample and the electrostatic actuator.

FIGS. 2A-2B show a model of a small sample pick up mechanism of an analyzing apparatus of the invention having an electrostatic actuator having a pair of needle-like members for grabbing a sample and driving to make the two pieces of needle-like members proximate to and remote from each other. The small sample pick up mechanism is of a type of grabbing the sample in a so-to-speak tweezers mode. FIG. 2A shows a structure aligning positions of two pieces of needle-like members $1a$, $1b$ at a center, arranging electrostatic actuator $2a$, $2b$ in a shape of a flat plate on both sides to interpose the two pieces of needle-like members $1a$, $1b$, and connecting the electrostatic actuators $2a$, $2b$ and the two pieces of needle-like members $1a$, $1b$ locally by coupling members. Inner side portions of the electrostatic actuators $2a$, $2b$ connected to the needle-like members $1a$, $1b$ by the coupling members constitute movable portions and outer side portions thereof constitute fixed portions. The tweezers mechanism is attached to a tip portion or the like of a manipulator in an observing apparatus or an analyzing apparatus and is provided with means for monitoring a change in an electrostatic capacitance between electrodes of the electrostatic actuators $2a$, $2b$ (electrostatic capacitance sensor). When the tweezers mechanism is moved by operating the manipulator and the needle-like members $1a$, $1b$ are brought into contact with a sample, a change in the electrostatic capacitance can be sensed by the monitor by reaction thereof to sense the contact. When the manipulator is stopped to operate at a location of sensing the contact and a voltage is supplied between the electrodes, the two pieces of needle-like members $1a$, $1b$ are moved in parallel with each other to be proximate to each other and the small sample can be pinched therebetween. When the sample is pinched by the tweezers mechanism, by operating the manipulator, the small sample is pulled to separate from the main body and is moved to a desired position.

A model shown in FIG. 2B differs from the previous model of FIG. 2A in adopting a constitution of connecting the needle-like probes $1a$, $1b$ and the electrostatic actuators $2a$, $2b$ by interposing insulating layers 3 therebetween, sides of the electrostatic actuators $2a$, $2b$ are grounded and sides of the needle-like probes $1a$, $1b$ are floated. An explanation will be given of a method of analyzing an electric property of a surface of the sample of the invention using the apparatus adopting such a constitution. First, portions of connecting the needle-like members $1a$, $1b$ and the electrostatic actuators $2a$, $2b$ are insulated and therefore, a test can be executed in a state in which a voltage or the like applied on an electrostatic actuator driving portion is not applied to the sample and the sample is not electrically damaged. An image of the surface of the sample is observed by a microscope function. Further, a measured portion of the sample is specified and the tips of the needle-like members $1a$, $1b$ are made to approach the position by operating the manipulator and the operation is executed while observing the image by the microscope. The image of the microscope is a two-dimensional image and therefore, even when the tip portions of the needle-like members $1a$, $1b$ look to overlap the specified portion, it cannot be confirmed whether the tip portions are brought into contact with the specified portions. However, according to the invention, there is provided the function of monitoring the electrostatic capacitance between the electrodes of the electrostatic actuator and therefore, it can be sensed that the tip portions of the needle-like members $1a$, $1b$ are brought into contact with the sample from the change in the electrostatic capacitance of the electrostatic actuator shown in the monitor when the front end portions are brought into contact with the sample. When the tip portions of the needle-like members $1a$, $1b$ are brought into contact with the surface of the sample, by confirming the contact, the electric property of the portion can easily and firmly be detected by a detecting portion electrically connected thereto via the needle-like members. For example, when a voltage is supplied to the needle-like members $1a$, $1b$ and the potential thereof is not lowered, it is known that the surface of the sample is constituted by a nonconductive member or floated up and when the potential is lowered to zero level, it is known that the portion is constituted by a conductive member and is grounded. In this way, the electric property of the surface of the sample can be analyzed. Although here, an explanation has been given of two pieces of needle-like structures as the probes, naturally, the probe used in the method of analyzing the electric property of the surface of the sample may comprise a single piece of needle-like member. An insulting portion in that case may be provided at a pertinent portion between the needle-like member and the actuator such as a root portion of the needle-like member.

EMBODIMENT 1

Figure 3:
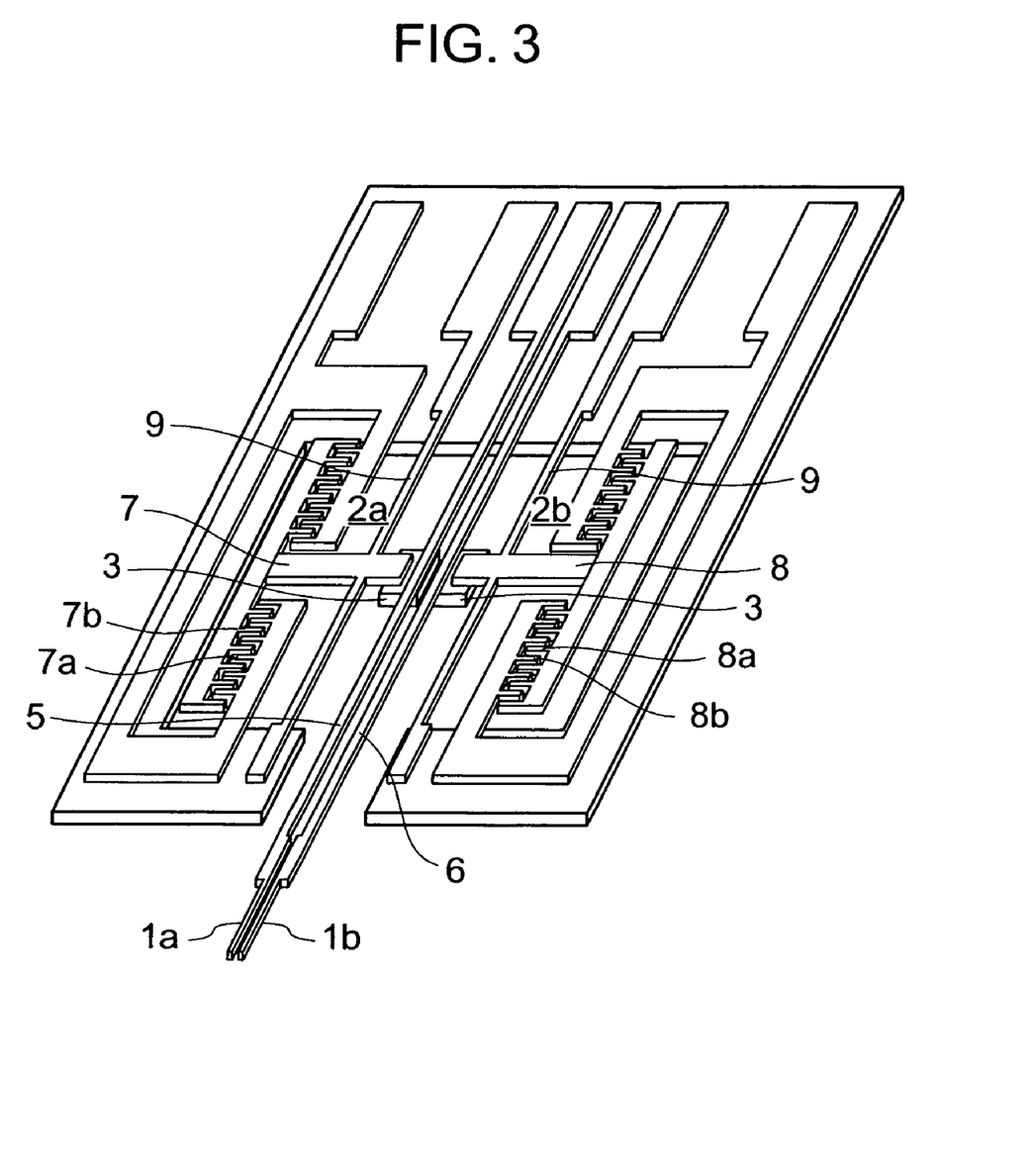
FIG. 3 is a view showing an embodiment of a grip of a pick up mechanism fabricated by a semiconductor silicon process technology.

FIG. 3 shows an embodiment of a gripper (tweezers) used in a pick up mechanism of the invention. The gripper is fabricated by a semiconductor silicon process technology. The gripper is basically constituted by a two layers structure, light gray designates silicon and dark gray designates silicon dioxide. The silicon dioxide portion comprises an insulating material and it is constituted by an integrated structure except the insulating portion 3 and functions as a board 4 fixedly attached with a conductive silicon layer. A center portion thereof is arranged with two pieces of rods 5, 6 to be substantially in parallel with each other, base portions of the rods are fixedly attached with the board 4, and tip sides therefrom are made to be free and the tip portions are integrally formed with the needle-like members 1a, 1b achieving a grabbing function. Center portions of the rods are connected with arms 7 (8) in a T-like shape directed to outer sides in an orthogonal direction via the insulating portions 3 in a block-like shape. Other end sides of the arms 7 (8) are formed with combteeth electrodes 7a (8a). Further, counter combteeth electrodes 7b (8b) are arranged to be opposed to the combteeth electrodes 7a (8a) to constitute a driving portion of the electrostatic actuator. Further, support members 9 are attached to vicinities of portions of the arms 7 (8) connected to the insulating portion 3, and base portions on other end sides of the support member 9 are integrally attached fixedly to the board 4. It will be known that the gripper is constituted by a structure of being symmetric in view from a center line of the two pieces of rods 5, 6. Further, when a voltage applied between the combteeth electrodes 7a (8a) and the combteeth electrodes 7b (8b) opposed thereto, an attraction force is operated between the two electrodes and the arms 7 (8) function as the electrostatic actuator for making the two pieces of rods 5, 6 proximate to each other. By making the two pieces of rods 5, 6 proximate to each other, also the needle-like members 1a, 1b at the tip portions are driven to be proximate to each other and when a body is present therebetween, the needle-like members 1a, 1b pinch the body. Further, when there is not the voltage between the two electrodes, the support members 9 are operated as leaf springs to pull back the arms 7 (8) in outer side directions and therefore, the body is released from being pinched by moving the needle-like members 1a, 1b in directions opposed to each other by way of the two pieces of rod needle-like members 1a, 1b. As explained above, the gripper achieves the tweezers function.

A simple explanation will be given of a method of fabricating the gripper by a semiconductor silicon process technology.

1) A resist film is formed on a surface of silicon of a silicon board comprising two layers of silicon oxide and silicon.
2) By using a mask in which a pattern of a silicon portion of light gray of FIG. 3 is drawn, the pattern is transcribed by exposing the resist film.
3) The resist film is removed by an exfoliating solution and the silicon layer is exposed at a portion other than the pattern.
4) When subjected to an etching treatment, the exposed silicon is removed and the layer of silicon oxide is exposed.
5) The silicon board is turned over and a resist film is formed on a surface of the silicon oxide layer.
6) By using a mask in which a pattern of the silicon oxide portion of dark gray of FIG. 3 (incidentally, a pattern is connected with patterns contiguous in a front and rear direction and in a left and right direction with pertinent distances therebetween), the pattern is transcribed by exposing the resist film. Further, at this occasion, positioning with the surface pattern is important.
7) The resist film is removed by an exfoliating solution and the silicon oxide layer is exposed at a portion other than the pattern.
8) When subjected to an etching treatment, the exposed oxide silicon portion is removed and the grippers of FIG. 3 are formed to be aligned in the front and rear direction and in the left and right direction.
9) The individual grippers are cut to separate and set to the analyzing apparatus.

The grippers are fabricated by the semiconductor silicon process technology in this way and therefore, a number of the grippers having the same standard can be provided in one process and therefore, the grippers can be supplied inexpensively.

Figure 4A:
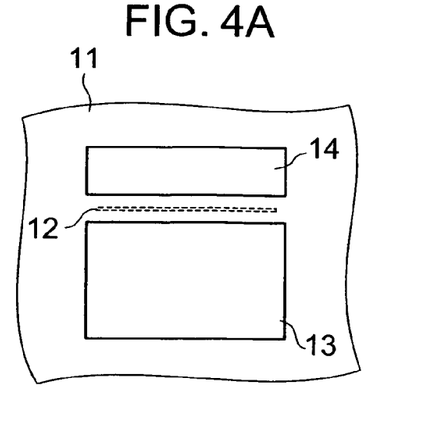
FIGS. 4A-4F illustrate views for explaining an operation of fabricating a TEM sample by an FIB apparatus integrated with the pick up mechanism of the invention.
Figure 4B:
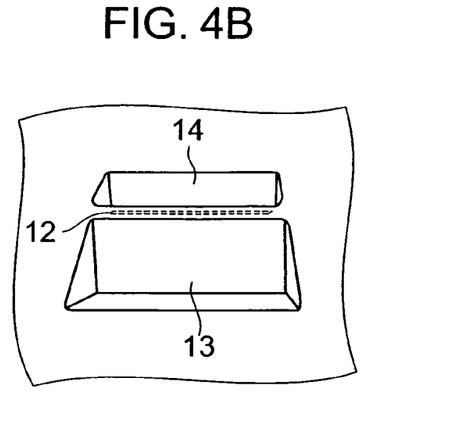
Figure 4C:
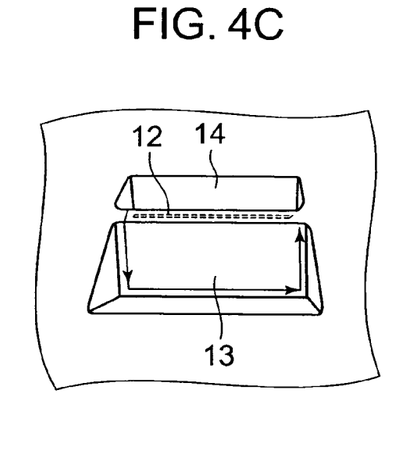
Figure 4D:
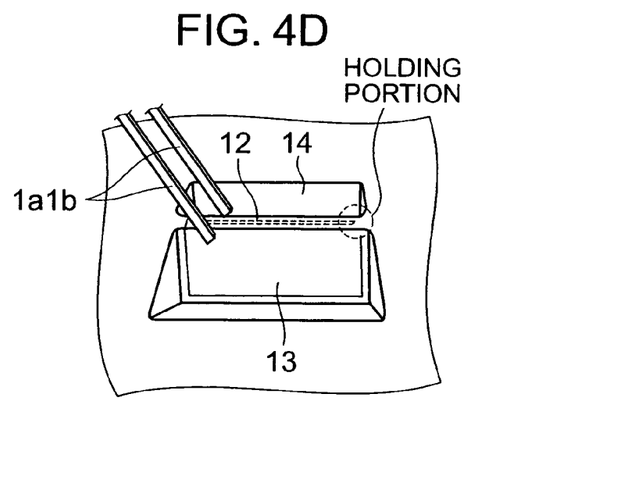
Figure 4E:
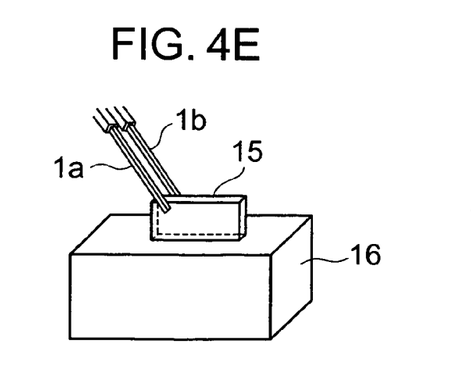
Figure 4F:
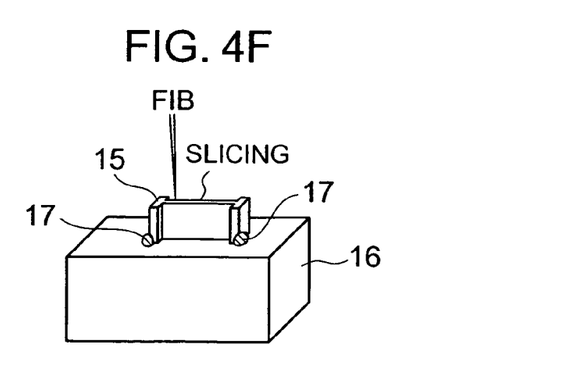

Next, an explanation will be given of a process of fabricating a sample of a sectional structure of a semiconductor device for observing by a transmission electron microscope (hereinafter, referred to as TEM sample) by using an FIB apparatus attached with the gripper at a tip portion of a micromanipulator in reference to FIG. 4. In FIG. 4A, a sectional portion 12 to be observed of a sample body 11 is specified by an image of the microscope and a front hole 13 and a rear hole 14 are bored in an order of, for example, a, b at two faces interposing the section in a region indicated by a broken line by FIB etching. FIG. 4B shows an image constituted by tilting a stage of the sample finished with boring and observing the sectional portion by the microscope from a skewed front direction. A thickness of the portion to be observed is several micrometers and is not a thickness of transmitting an electron beam. Next, as shown by FIG. 4C, FIB is irradiated from a skewed front direction to cut a periphery of the region to be observed. For example, as designated by notation c, a side thereof is cut, successively, as designated by notation d, a bottom thereof is cut, further, a side is cut as designated by notation e. At this occasion, it is preferable to constitute a holding portion without cutting a portion thereof to support the sample piece such that the sample piece is not fallen down. Although the operation up to this stage remains unchanged from that of the background art, in the background art, at this stage, the tip of the probe is made to approach a shoulder portion of the portion to be observed while operating the manipulator while observing the portion to be observed by the microscope and when the tip is brought into contact with the shoulder portion, there is carried out an operation of fixedly attaching the tip of the probe and the sample piece by CVD by FIB. Although this is a troublesome operation requiring considerable skill, according to the invention, there is provided the function of monitoring the change in the electrostatic capacitance between the electrodes of the electrostatic actuator by the sensor and therefore, as shown by FIG. 4D, when the needle-like member at the tip of the gripper is brought into contact with the sample, the electrostatic capacitance is changed and the contact can be confirmed. The operation of making the needle-like member approach the predetermined position of the sample by operating the manipulator while observing the image of the microscope is significantly facilitated. When the two piece of needle-like members are brought to the position for pinching the sample piece, the sample is pinched thereby by driving the electrostatic actuator by applying the voltage between the two electrodes. The operation is carried out by simply applying the voltage and the operation of fixedly attaching the needle-like members and the sample piece by CVD is not needed. Successively, the uncut holding portion is cut by irradiating FIB to cut out and the sample piece is picked up. The sample piece is carried onto a prepared sample base 15 by operating the manipulator. When the sample piece is mounted on the sample base 15, the sample piece is fixed thereto at portions 17 by CVD using FIB. Further, the sample piece is released from being held by releasing the voltage applied to the electrostatic actuator. The operation may be carried out by simply stopping to apply the voltage and the operation is significantly easier than the operation of cutting off the tip portion of the probe and the sample piece by irradiating FIB in the background art. Finally, as shown by FIG. 4F, by FIB etching, the sample piece is remachined to subject the sample piece to slicing to constitute the TEM sample.

What is claimed is:

1. A pick-up device comprising:
a pair of fingers operable to pick up a sample under observation by a microscope;
a transporter configured to transport the fingers relative to the sample;
at least one actuator configured to operate at least one of the fingers to change a relative distance between the fingers, wherein the actuator comprises a pair of electrodes one of which is movable relative to the other and operably connected to one finger to move the finger relative to the other; and
an electric charger configured to electrically charge the pair of electrodes to the same polarity to move one electrode relative to the other of the pair.

2. A pick-up device according to claim 1, wherein the charger is also configured to charge the pair of electrodes to the opposite polarities.

3. A pick-up device according to claim 1, wherein the actuator further comprises a return spring to return one finger relative to the other after the finger is moved relative to the other by the charged at least one electrode.

4. A pick-up device according to claim 1, wherein the pair of electrodes comprises at least one pair of opposite surfaces.

5. A pick-up device according to claim 4, wherein the surfaces are opposite to each other in an interdigitized pattern.

6. A pick-up device according to claim 1, wherein the electrode which is operably connected to the finger is electrically isolated from the finger.

7. A pick-up device according to claim 1, wherein the other of the electrode which is operably connected to the finger is electrically grounded.

8. A pick-up device according to claim 1, wherein the microscope is a transmission electron microscope.

9. A pick-up device according to claim 1, wherein the microscope is a scanning probe microscope.

10. A pick-up device according to claim 1, further comprising a sensor configured to monitor a capacitance between the pair of electrodes to detect a change of the capacitance between the electrodes.

11. A pick-up device according to claim 10, wherein the sensor monitors the capacitance, which is determinable based on a relative distance between the electrodes.

12. A pick-up device according to claim 11, wherein the sensor detects a change of the capacitance caused by a change of the relative distance between the electrodes which is caused by a contact of the finger with the sample.

13. A pick-up device according to claim 10, wherein the fingers are made electrically neutral so that a contact by the fingers with the sample will not cause any current flow through the sample.

14. A pick-up device according to claim 10, further comprising a power source responsive to a contact by the fingers with the sample to create an electrical potential between the fingers to determine electrical characteristics of the sample.

15. A pick-up device comprising:
a pair of fingers operable to pick up a sample under observation by a microscope;
a transporter configured to transport the fingers relative to the sample;
at least one actuator configured to operate at least one of the fingers to change a relative distance between the fingers, wherein the actuator comprises a pair of electrodes one of which is movable relative to the other and operably connected to one finger to move the finger relative to the other;
an electric charger configured to electrically charge at least one of the electrode pair to move one electrode relative to the other of the pair; and
a return spring configured to return one finger relative to the other after the finger is moved relative to the other by the charged at least one electrode.

16. A pick-up device according to claim 15, wherein the charger is configured to charge the pair of electrodes to the opposite polarities.

17. A pick-up device according to claim 15, wherein the charger is configured to charge the pair of electrodes to the same polarity.

18. A pick-up device according to claim 15, wherein the pair of electrodes comprises at least one pair of opposite surfaces.

19. A pick-up device according to claim 15, wherein the surfaces are opposite to each other in an interdigitized pattern.

20. A pick-up device according to claim 15, wherein the electrode which is operably connected to the finger is electrically isolated from the finger.

21. A pick-up device according to claim 15, wherein the other of the electrode which is operably connected to the finger is electrically grounded.

22. A pick-up device according to claim 15, wherein the microscope is a transmission electron microscope.

23. A pick-up device according to claim 15, wherein the microscope is a scanning probe microscope.

24. A pick-up device according to claim 15, further comprising a sensor configured to monitor a capacitance between the pair of electrodes to detect a change of the capacitance between the electrodes.

25. A pick-up device according to claim 24, wherein the sensor monitors the capacitance, which is determinable based on a relative distance between the electrodes.

26. A pick-up device according to claim 25, wherein the sensor detects a change of the capacitance caused by a change of the relative distance between the electrodes which is caused by a contact of the finger with the sample.

27. A pick-up device according to claim 24, wherein the fingers are made electrically neutral so that a contact by the fingers with the sample will not cause any current flow through the sample.

28. A pick-up device according to claim 24, further comprising a power source responsive to a contact by the fingers with the sample to create an electrical potential between the fingers to determine electrical characteristics of the sample.

* * * * *